Figure 1:
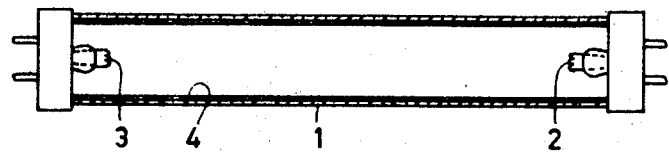

United States Patent [19]

Konijnendijk et al.

[11] 4,354,139
[45] Oct. 12, 1982

[54] LOW-PRESSURE MERCURY VAPOR DISCHARGE LAMP

[75] Inventors: Willem L. Konijnendijk; Robert C. Peters; Petrus J. M. Willemsen, all of Eindhoven, Netherlands

[73] Assignee: U.S. Philips Corporation, New York, N.Y.

[21] Appl. No.: 137,890

[22] Filed: Apr. 7, 1980

[30] Foreign Application Priority Data

Jul. 3, 1979 [NL] Netherlands .......................... 7905161

[51] Int. Cl.³ ............................................ C09K 11/46
[52] U.S. Cl. ..................................... 313/486; 313/221; 313/493
[58] Field of Search ......................... 313/221, 486, 493

[56] References Cited

U.S. PATENT DOCUMENTS 3,715,612  2/1973  Someya et al. ...................... 313/486
4,153,572  5/1979  Wolfe ............................... 313/486 X
4,215,289  7/1980  Dettair et al. ....................... 313/486

Primary Examiner—Paul L. Gensler
Attorney, Agent, or Firm—Robert S. Smith

[57] ABSTRACT

A low-pressure mercury vapor discharge lamp for radiation purposes having a discharge tube made of glass with selective transmission, the tube being coated on the inside with a luminescent layer. This layer contains a luminescent material which has the characteristic line emission of gadolinium at 312 nm. The discharge tube is made of glass having an absorption edge located between 260 and 280 nm and the tube has at 312 nm a transmission of at least 80%.

8 Claims, 2 Drawing Figures

LOW-PRESSURE MERCURY VAPOR DISCHARGE LAMP

The invention relates to a low-pressure mercury vapour discharge lamp for radiation purposes having a discharge tube made of glass with selective transmission, the tube being coated on the inside with a luminescent layer.

It is known that radiation in the wavelength range from 305–320 nm may have a favorable therapeutical effect, for example in the treatment of psoriasis and other skin diseases (see the article by H. Tronnier et al in Afinidad, May 1977, pages 285–290). A lamp of the type defined in the opening paragraph, intended to radiate selectively in the above-mentioned wavelength range is disclosed in the German Patent Application 2,707,894 which has been laid open to public inspection. The known lamp is provided with a luminescent layer of a luminescent, cerium-activated strontium aluminate. This luminescent material, which is further described in Netherlands Patent Application 7214862 and 7401935 has a comparatively wide emission band (half-value width approximately 45 nm) with a maximum at approximately 310 nm, so that approximately half of the radiation emitted by this material is located in the UVB-portion of the erythema range (290–315 nm). At the maximum erythema sensitivity (approximately 297 nm) the intensity of this material is still approximately 75% of the peak value at 310 nm. As, generally, only a minute quantity of erythema radiation is permissible for photo-therapy, a filter is used in the known lamp. For this reason, the discharge tube having the luminescent layer is made of glass having a selective transmission. Specifically, this glass must have an absorption edge at approximately 295 nm, that is to say there is substantially no transmission below 295 nm.

The known lamp has the serious drawback that the radiation efficiency is very low, as more than 60% of the radiation emitted by the luminescent material is absorbed by the wall of the discharge tube. It furthermore appears that the selectivity of the radiation emitted by the lamp is not very high. It appeared, namely, that for each watt of total radiation emitted in the UV region (250–400 nm) the lamp produces only 0.14 watt of useful radiation in the range from 307.5 to 317.5 nm. Consequently, long irradiation times are necessary, with all the drawbacks this entails. A further drawback of the known lamp, also owing to the poor selectivity, is that the erythema radiation emitted by the lamp is considerably above the minimum quantity which is theoretically possible. Since, namely, the erythema sensitivity curve (as defined by the Commission Internationale d l'Eclairage) in the range from 307.5 to 317.5 nm still has values ranging from 20% to almost 0%, radiation in this wavelength range also shows erythema activity. Radiation having, for example, an equienergy spectrum has, in this range, per watt approximately 0.08 erythema watt per watt of useful radiation, which is then the lowest quantity which can be obtained. However, the known lamp appears to radiate approximately 0.17 erythema watt per watt of useful radiation. For a given permissible erythema load, this means a limitation of the dose of useful radiation per treatment and, consequently, an increase in the number of treatments required.

It is an object of the invention to provide a lamp for radiation purposes having a high radiation efficiency and a highly improved selectivity.

According to the invention, a low-pressure mercury vapour discharge lamp for radiation purposes having a discharge tube made of glass with selective transmission, the tube being coated on the inside with a luminescent layer, is characterized in that the luminescent layer contains a luminescent material which shows the characteristic line emission of gadolunium at 312 nm, and that the discharge tube is made of glass having an absorption edge located between 260 and 280 nm, the tube having a transmission of at least 80% at 312 nm.

The invention is based on the recognition of the fact that a high radiation efficiency and a high selectivity can only be obtained when very severe requirements are imposed on the luminescent material to be used. In addition to a high efficiency on excitation by 254 nm radiation, the material must have an emission which is substantially wholly concentrated in the range from 305–320 nm, substantially all the radiation emitted by the material then namely being useful radiation, and a filter having an absorption edge at approximately 295 nm (so comparatively close to the lower limit of the range of desired radiation) to limit the erythema radiation then not being necessary. It appeared that materials having gadolinium emission satisfy these conditions perfectly. The Gd-ion has a characteristic emission spectrum, that is to say the spectrum is only little dependent on the host lattice in which the luminescent ion is incorporated. The Gd-emission consists of a very narrow band (actually some closely adjacent emission lines) with a maximum at approximately 312 nm. The half-width value of this emission band is only 2 to 4 nm. Furthermore the Gd-luminescence appears to occur very efficiently in different host lattices.

Although an absorption filter for erythema radiation is superfluous in a lamp according to the invention the discharge tube must yet have a selective transmission. Specifically, the glass of this tube must have an absorption edge located between 260 and 280 nm. This means that the transmission curve of the glass at a wavelength in the range from 260 to 280 nm reaches a value of 10%, and still lower values below that wavelength. This guarantees that substantially no radiation is transmitted below 260 nm. Furthermore, the glass tube must have at 312 nm a transmission of at least 80%. The said transmission properties are necessary to prevent the mercury-resonance radiation produced in the lamp at 185 nm and predominantly at 254 nm, from passing to the outside. The requirement that there is at least a transmission of 80% at 312 nm ensures that the transmission curve varies sufficiently steeply and that the majority of the Gd-radiation is transmitted.

With a lamp according to the invention it is possible to obtain a high radiation efficiency as not more than 20%, and at an optimum choice of the glasses for the discharge tubes a still much lower quantity, of the radiation emitted by the luminescent material is absorbed by the tube wall. This is a considerable improvement compared with the known lamp, in which more than 60% of the radiation is absorbed. A further considerable advantage of a lamp according to the invention is its excellent selectivity. Instead of the emitted radiation of the known lamp of only 0.14 watt of useful radiation (307.5–317.5 nm) per watt in the UV (250–400 nm), this fraction of useful radiation is a factor of 5 to 6 higher, namely 0.70 to 0.80 watt per watt in a lamp according to the invention. The very good selectively of the lamp is also apparent from the low fraction of erythema radiation which, depending on the glass opted for appears namely to be only 0.10 to 0.13 erythema watt per watt of useful radiation, which values approach the theoretically possible minimum quantities very closely.

An embodiment of a lamp according to the invention, which is preferred, is characterized in that the luminescent layer contains a borate, activated by Gd and Bi and defined by the formula $La_{1-x-y}Gd_xBi_yB_3O_6$, wherein $0.15 \leq x$, $0.001 \leq y \leq 0.05$ and $x+y \leq 1$. Those borates which are further described in the Netherlands Patent Application 7607724, which has been laid open to public inspection, emit very efficiently the characteristic Gd-radiation. On excitation by the mercury resonance radiation having a wavelength of approximately 254 nm, quantum efficiencies of 70 to 75% can be obtained with these materials.

A second advantageous embodiment of a lamp according to the invention is characterized in that the luminescent layer contains a ternary aluminate activated by Gd and Pb and having a hexagonal magnetoplumbite structure, the aluminate having the composition ABC, wherein A represents 25-99 mole % $\frac{1}{2}$ $Gd_2O_3$, 1-35 mole % PbO and, possibly, $\frac{1}{2}$ $La_2O_3$, wherein B represents $Al_2O_3$, not more than 20 mole % of the $Al_2O_3$ having been replaced by $Sc_2O_3$, and wherein C represents MgO and/or ZnO, up to 10 mole % of the $Al_2O_3$ possibly having been replaced by an equivalent quantity of $SiO_2$ together with MgO and/or ZnO, up to 70 mole % of A possibly having been replaced by SrO and/or CaO and, simultaneously, an equivalent quantity of C by $\frac{1}{2}$ $Al_2O_3$, and wherein the contents A, B and C satisfy the conditions $[A] \geq 0.02$, $0.55 \leq [B] \leq 0.95$ and $[C] \geq \frac{1}{2}[A]$. These luminescent aluminates are further described in the Netherlands Patent Application 7811436 (PHN 9288), which has not yet been laid open to public inspection, and appear to have high quantum efficiencies. The materials defined by the formulae $Gd_{0.90}Pb_{0.15}MgAl_{11}O_{19}$ and $Gd_{0.88}Pb_{0.18}ZnAl_{11}O_{19}$, for example, have a quantum efficiency (254 nm-excitation) of 50 to 55%.

A further preferred embodiment of a lamp according to the invention is characterized in that the luminescent layer contains a silicate of Sr and/or Ca and of Y and/or La and activated by Gd and Pb defined by the formula $(Sr, Ca)_{3-p}Pb_p(Y,La)_{2-q}Gd_qSi_6O_{18}$, wherein $0.01 \leq p \leq 0.50$ and $0.05 \leq q \leq 2.0$. At 254 nm-excitation, these silicates have a quantum efficiency for the Gd luminescence of approximately 60%.

It is conceivable that quartz glass or a glass consisting predominantly of $SiO_2$ is used as the glass for the discharge tube of a lamp according to the invention, the absorption edge having been shifted to the range from 260 to 280 nm by the addition of small quantities of other elements.

Preference is, however, given to a low-pressure mercury vapour discharge lamp according to the invention, the glass of its discharge tube containing
68-83 mole % $SiO_2$,
2.5-3.0 mole % $B_2O_3$,
16-20 mole % of at least an alkali metal oxide,
2.6-3.3 mole % of at least an alkaline earth metal oxide,
0-2.0 mole % $Al_2O_3$,
and furthermore at least one of the oxides $TiO_2$, $CeO_2$, CuO, $Fe_2O_3$ and $V_2O_5$ in a small quantity, such that the absorption edge of the glass is located between 260 and 280 nm. The glasses whose basic composition is given here in mole % and for which chemically pure materials must be used have a very short-wave absorption edge, for example at 210 nm, so that they pass ultra-violet radiation up to relatively short wave-lengths. By the addition of a minute quantity of one or more of the oxides $TiO_2$, $CeO_2$, CuO, $Fe_2O_3$ and $V_2O_5$ to such a basic composition, the absorption edge of the glass can be adjusted between comparatively wide limits. According as the quantity used of the above oxides is greater the absorption edge will be found at longer wavelengths. The glasses to be used for the lamps according to the invention generally contain from 100 to 2500 ppm by weight of the said oxides. These glasses have the further advantage that they have a transmission curve which varies sufficiently steeply so that the majority of the desired useful radiation is transmitted. Furthermore, these glasses have suitable properties for their manufacture into tubes for low-pressure mercury vapour discharge lamps.

A particularly advantageous glass composition for the discharge tube of a low-pressure mercury vapor discharge lamp according to the invention consists of
$75.5 \pm 2$ mole % $SiO_2$
$2.8 \pm 0.1$ mole % $B_2O_3$
$10.2 \pm 0.3$ mole % $Na_2O$
$7.7 \pm 0.3$ mole % $K_2O$
$3.0 \pm 0.1$ mole % BaO
$1.0 \pm 0.03$ mole % $Al_2O_3$, and, in addition, of 500-2000 ppm by weight of $TiO_2$.

Embodiments of lamps according to the invention will now be further described with reference to a drawing and a number of measurements.

In the drawing

Figure 2:
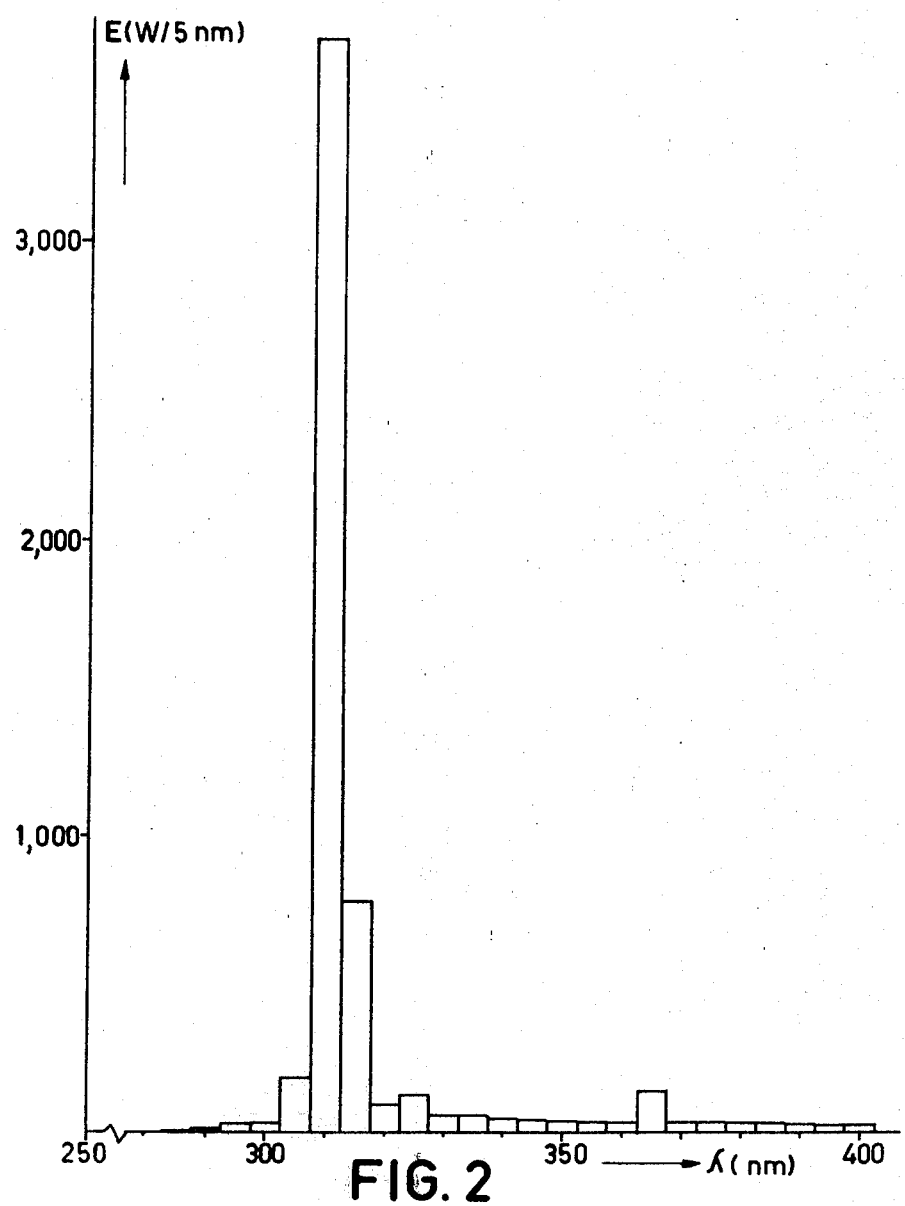

FIG. 1 shows schematically and in cross-sectional view a lamp according to the invention and FIG. 2 shows by means of a graph the spectral energy distribution of the emitted radiation of such a lamp.

The lamp shown in FIG. 1 has a glass discharge tube 1 which is approximately 120 cm long and has an outside diameter of approximately 38 mm. The wall thickness of the tube 1 is approximately 0.75 mm. The glass of the tube has the following compositions:
75.46 moles % (68.4% by weight) $SiO_2$,
2.76 mole % (2.9% by weight) $B_2O_3$,
10.17 mole % (10.9% by weight) $Na_2O$,
7.68 mole % (10.9% by weight) $K_2O$,
2.94 mole % (6.8% by weight) BaO,
0.97 mole % (1.5% by weight) $Al_2O_3$,
900 wt. ppm $TiO_2$.
At approximately 265 nm this glass has a transmission of 10%. At 312 nm the transmission of the tube is 85 to 90%. Electrodes 2 and 3 are provided, one at each end of the lamp, the discharge taking place during operation between these electrodes. The lamp contains a mixture of rare gases as the starting gas, and a small quantity of mercury. On the inside the tube 1 is coated with a luminescent layer 4 comprising a luminescent material which emits the characteristic 312 nm radiation of Gd. The layer 4 can be applied in a customary manner to the tube 1, for example by means of a suspension containing the luminescent material. During operation the lamp consumes a power of 40 W.

EXAMPLE 1:

A number of lamps of the type shown in FIG. 1 were coated with a layer of luminescent borate defined by the formula $La_{0.487}Gd_{0.5}Bi_{0.013}B_3O_6$. After having been in operation for 100 hours it appeared that these lamps emitted over the whole spectrum (from 250-400 nm) a quantity of radiation totaling 5.603 W. The quantity of useful radiation in the range from 307.5 to 317.5 nm appeared to be 4.460 W, that is to say approximately 80% of the total emitted radiation is useful radiation. FIG. 2 is a graphical representation of the spectral energy distribution of the radiation emitted by this lamp. The wavelength λ in nm is plotted on the horizontal axis, the emitted radiant energy E being plotted on the vertical axis in W per wavelength interval of 5 nm.

EXAMPLE 2:

Lamps having a construction as described with reference to FIG. 1 but having a 150 cm long tube and intended to consume a power of 80 W, were coated with a luminescent layer of the same luminescent material as used in example 1. After having been in operation for 100 hours a total (250–400 nm) emitted quantity of radiation of 11.2 W was measured on these lamps. It appeared that 8.0 W (71.5%) was emitted in the range from 307.5–317.5 nm. The quantity of erythema radiation emitted by the lamp appeared to be 0.92 erythema watt, that is to say only approximately 11.5% of the total quantity of useful radiation. For comparison, the known lamps having a construction equal to the lamps described above but made of glass having an absorption edge at approximately 300 nm and containing a luminescent cerium-activated strontium aluminate, emit in total (250–400 nm) a radiation of 5.9 W (that is only approximately 33% of the radiation generated in the luminescent material). However, only approximately 0.83 W (that is to say approximately 14%) of this quantity of radiation is located in the range from 307.5–317.5 nm. In addition, it appeared that the quantity of erythema radiation emitted by the known lamp was 16.7% of the quantity of useful radiation (namely approximately 0.14 erythema watt).

When the lamps according to the invention are used it is therefore possible to choose the radiation time a factor of 10 shorter for the same dose of useful radiation, while the erythema dose is reduced by approximately 35%.

EXAMPLE 3:

A number of lamps of the type shown in FIG. 1 were coated with a luminescent layer of a luminescent silicate defined by the formula $Sr_{2.9}Pb_{0.1}LaGdSi_6O_{18}$. After having been in operation for 100 hours a quantity of radiation of 4.96 W, emitted over the whole ultraviolet portion of the (250–400 nm) spectrum was measured on these lamps. It appeared that 3.95 W thereof was emitted in the range from 307.5 to 317.5 m,. It appeared that for these lamps the spectral energy distribution of the emitted radiation was substantially equal to those of the lamps described in example 1.

What is claimed is:

1. A low-pressure mercury vapour discharge lamp for radiation purposes having a discharge tube made of glass with selective transmission, the tube being coated on the inside with a luminescent layer, characterized in that the luminescent layer contains a luminescent material which has the characteristic line emission of gadolinium at 312 nm, and that the discharge tube is made of glass having an absorption edge located between 260 and 280 nm, the tube having at 312 nm a transmission of at least 80%.

2. A low-pressure mercury vapor discharge lamp as claimed in claim 1, characterized in that the luminescent layer contains a borate activated by Gd and Bi, this borate being defined by the formula $La_{1-x-y}Gd_xBi_yB_3O_6$, wherein $0.15 \leq x$, $0.0001 \leq y \leq 0.05$ and $x+y \leq 1$.

3. A low-pressure mercury vapor discharge lamp as claimed in claim 1, characterized in that the luminescent layer contains a ternary aluminate activated by Gd and Pb and having the hexagonal magneto-plumbite structure, the aluminate having the composition ABC, wherein A represents from 25–99 mole % $\frac{1}{2}Gd_2O_3$, 1–35 mole % PbO and, 0–74 mole percent $\frac{1}{2}Ca_2O_3$, wherein B represents $Al_2O_3$, not more than 20 mole % of the $Al_2O_3$ having been replaced by $Sc_2O_3$ and wherein C represents at least one compound from the group consisting of MgO and ZnO, the contents A, B and C satisfying the conditions $[A] \geq 0.02$, $0.55 \leq [B] \leq 0.95$ and $[C] \geq \frac{1}{2}[A]$.

4. A low-pressure mercury vapor discharge lamp as claimed in claim 1, characterized in that the luminescent layer contains a Gd and Pb-activated silicate of at least one element from the group consisting of Sr and Ca and of at least one element from the group consisting of Y and La defined by the formula $(Sr, Ca)_{3-p}Pb_p(Y, La)_{2-q}Gd_qSi_6O_{18}$, wherein $0.01 \leq p \leq 0.50$ and $0.05 \leq q \leq 2.0$.

5. A low-pressure mercury vapor discharge lamp as claimed in claim 1, 2, 3 or 4, characterized in that the glass of the discharge tube contains 68–83 mole % $SiO_2$,
2.5–3.0 mole % $B_2O_3$,
16–20 mole % of at least an alkali metal oxide,
2.6–3.3 mole % of at least an alkaline earth metal oxide.
0–2.0 mole % $Al_2O_3$, and further at least one of the oxides $TiO_2$, $CeO_2$, CuO, $Fe_2O_3$ and $V_2O_5$ in a small quantity, thus, that the absorption edge of the glass is between 260 and 280 nm.

6. A low-pressure mercury vapor discharge lamp as claimed in claim 5, characterized in that the glass consists of 75.5±2 mole % $SiO_2$
2.8±0.1 mole % $B_2O_3$
10.2±0.3 mole % $Na_2O$
7.7±0.3 mole % $K_2O$
3.0±0.1 mole % BaO
1.0±0.03 mole % $Al_2O_3$ and, in addition, 500–2000 wt. ppm $TiO_2$.

7. A low-pressure mercury vapor discharge lamp as claimed in claim 3, wherein up to 10 mole % of the $Al_2O_3$ is replaced by an equivalent quantity of $SiO_2$ together with a material selected from the group consisting of MgO and ZnO.

8. A low-pressure mercury vapour discharge lamp as claimed in claims 3 or 7, wherein up to 70 mole % of A is replaced by a material selected from the group consisting of SrO and CaO and, simultaneously, an equivalent quantity of C by $\frac{1}{2}Al_2O_3$.

* * * * *